United States Patent
Stein (12)

(10) Patent No.: US 6,403,068 B1
(45) Date of Patent: Jun. 11, 2002

(54) REFLECTIVE CREAM FOR PEDESTRIANS

(76) Inventor: Julie Anne Stein, 19158 Golden Meadow Way, Noblesville, IN (US) 46060

( * ) Notice: Subject to any disclaimer, the term of this patent is extended or adjusted under 35 U.S.C. 154(b) by 0 days.

(21) Appl. No.: 09/643,293

(22) Filed: Aug. 22, 2000

(51) Int. Cl.$^7$ ................................................. A61K 7/32
(52) U.S. Cl. ...................... 424/65; 252/301.17; 426/66; 435/189
(58) Field of Search ...................... 252/301.17; 424/65; 426/66; 435/189

(56) References Cited

U.S. PATENT DOCUMENTS

| | | | | |
|---|---|---|---|---|
| 4,049,792 A | * | 9/1977 | Elsnau | 424/66 |
| 4,533,489 A | | 8/1985 | Utts et al. | 252/301.17 |
| 5,317,098 A | | 5/1994 | Shizuya et al. | 536/23.1 |
| 5,789,471 A | | 8/1998 | Caruso | 524/161 |
| 5,876,995 A | * | 3/1999 | Bryan | 435/189 |
| 5,877,310 A | | 3/1999 | Reddington et al. | 536/25.32 |
| 5,942,216 A | * | 8/1999 | Herb et al. | 424/70.28 |
| 5,997,850 A | * | 12/1999 | Tang et al. | 424/65 |
| 6,008,373 A | | 12/1999 | Waggoner et al. | 548/427 |
| 6,025,431 A | | 2/2000 | Cardinali et al. | 524/547 |
| 6,033,651 A | | 3/2000 | Dolak et al. | 424/65 |
| 6,090,919 A | | 7/2000 | Cormack et al. | 530/350 |

* cited by examiner

Primary Examiner—Jose' G. Dees
Assistant Examiner—Robert M DeWitty
(74) Attorney, Agent, or Firm—Woodard, Emhardt, Naughton, Moriarty & McNett

(57) ABSTRACT

A brightly colored composition that me be quickly applied to a person's skin to increase their visibility while exercising or travelling by foot, bicycle, or the like. The composition includes a base carrier medium such as a lotion, cream, gel or the like having a coloring agent dissolved or otherwise dispersed therein. The composition also includes an antiperspriant to minimize degradation due to excessive sweating while exercising.

8 Claims, No Drawings

REFLECTIVE CREAM FOR PEDESTRIANS

TECHNICAL FIELD OF THE INVENTION

The present invention relates generally to safety gear and, more particularly, to a brightly colored body cream or paste for increasing the visibility of a pedestrian.

BACKGROUND OF THE INVENTION

Pedestrians such as walkers, joggers, runners, skateboarders, skaters, and cyclists run the risk of being hit by motorists who don't see them. This risk, while greatest at night, constantly accompanies anyone who uses streets and/or sidewalks for non-motorized transportation. Pedestrians often wear brightly colored or reflective clothing to make themselves more visible. However, this is only effective in situations where the pedestrians know ahead of time that they are going to be traveling the streets under their own power and are able to dress accordingly. Further, some of the visibility-enhancing clothing, such as shoes with battery powered lights included therein, are prohibitively expensive. Moreover, some pedestrians, such as serious runners and athletes, prefer to run or exercise while wearing as little clothing as possible, especially in hot weather. There is therefore a need for a method of increasing the visibility of a pedestrian to a passing motorist that may be easily carried and quickly utilized by a pedestrian. The present invention addresses this need.

SUMMARY OF THE INVENTION

The present invention relates to a brightly colored or fluorescent compound, such as a paste, gel, cream or the like, that can be quickly applied to a person's skin to increase their visibility to passing motorists. One form of the present invention is a water-removable chromophoric compound including an antiperspirant agent. The antiperspirant agent minimizes dilution, dissolution, degradation or other removal of the chromophoric compound due to, for example, sweating.

One object of the present invention is to provide improved visibility to pedestrians. Related objects and advantages of the present invention will be apparent from the following description

DETAILED DESCRIPTION OF THE PREFERRED EMBODIMENT

For the purposes of promoting an understanding of the principles of the invention, reference will now be made to the embodiment and specific language will be used to describe the same. It will nevertheless be understood that no limitation of the scope of the invention is thereby intended, such alterations and further modifications in the illustrated method and composition, and such further applications of the principles of the invention as illustrated therein being contemplated as would normally occur to one skilled in the art to which the invention relates.

The present invention relates to a visibility-enhancing composition, including a reflective body paint or colorant, or other make-up, for pedestrians. As used herein, the term pedestrian includes, but is not limited to, walkers, joggers, runners, skateboarders, skaters, cyclists and people confined to wheelchairs. Although the present invention is advantageously utilized by pedestrians, it is realized that the composition may be used in other cases where increased visibility is desired, such as by rock or mountain climbers, by lost or injured hikers, by hunters, or by concert attendees. In one form of the invention, the composition is a make-up that includes a carrier medium, a visibility-enhancing chromophore or colorant, and an active antiperspirant agent.

The carrier medium of the present invention is characterized as any substance capable of being applied to human skin as a layer or film and also capable of containing a substantially homogeneous distribution of a colorant in sufficient concentration to brightly color the wearer. The carrier medium is preferably readily removable from the skin through washing with soap and water, and is more preferably readily removable through washing with water alone. The carrier medium is also preferably removable from clothing through washing with detergent and water.

The carrier medium may be a gel, a lotion, a cream, a suspension, an emulsion or any other similar convenient medium known in the art. The carrier medium is preferably a liquid, but may also be a spreadable solid. The carrier medium may comprise from about 10% to 90% by weight of the composition. Some factors influencing the weight percent of the carrier medium include, but are not limited to, the viscosity of the carrier medium, the capacity of the carrier medium to contain a dye or chromophore, the color of the chromophore, and the brightness or reflectivity of the chromophore. The viscosity of the carrier medium may be increased (i.e., the carrier medium thickened), by any convenient technique known to one skilled in the art, such as through the additions of salts of fatty acids or other the like. For example, a propylene glycol carrier medium may be thickened through the addition of sodium stearate. The carrier medium preferably has a viscosity of about 1000 to 100,000 centipoise, and more preferably from about 2500 to 20,000 centipoise, although the carrier medium may have any viscosity sufficient to produce a durable skin coating imparting a bright color to the wearer.

The carrier medium is also preferably substantially durable, having sufficient viscosity, tackiness, surface tension and consistency to form a film on the skin that will survive through at least about a half hour of vigorous exercise, such as running, jogging, cycling or the like. Examples of suitable carrier media include glycerin, water-soluble silicone-glycol copolymers, propylene glycol-based lotions, oil-in-water emulsions, and polysaccharide gellant as described, for example, in U.S. Pat. No. 6,033,651 to Dolak et al.

The visibility-enhancing colorant or chromophore is characterized as any coloring agent or dye known in the art that may be dissolved, dispersed, or otherwise substantially homogeneously distributed in the carrier medium so as to impart a bright color to a wearer when the carrier medium is externally applied as a coating. If necessary, the solubility of a particular chromophore may be modified through the addition of an appropriate radical group as know in the art, such as, for example, adding hydrophilic group to the chromophore to increase the solubility of the chromophore in water. Generally, the chromophore comprises about 1 to 60 by weight percent of the composition; however, the amount of chromophore may as a function of its intensity or strength as a pigment and/or of its color. For example, the chromophore component may only be 5–15 weight percent to provide adequate coloration for a very intense chromophore, while the composition might require 40–60 weight percent of a less-vibrant chromophore.

The chromophore is preferably water soluble, although any convenient chromophore known to one skilled in the art that may be selected for addition to a suitable carrier medium. More preferably, the chromophore is not substantially reactive with the skin, such that the chromophore is easily removed upon washing the carrier medium off of the skin. Also, the chromophore is preferably substantially nontoxic when applied topically and/or ingested, such as, for example, a food dye. The chromophore is also preferably chosen to impart a bright color, such as orange, yellow, red, pink, purple or green, but any bright color may be chosen. Alternately, chromophores having the properties of fluorescence, bioluminescence, phosphorescence (i.e., "glow in the dark"), or the like may be selected. Bioluminescent compounds such as luciferins/luciferases, organic compounds found in fire flies and some deep sea fish and fluorescent compounds are well known to those skilled in the art. In addition to food dyes, other examples of suitable chromophores or coloring agents include water soluble glycoconjugated fluorescent labeling reagents as described, for example, in U.S. Pat. No. 5,877,310 to Reddington et al., and bioluminescent compounds as described, for example, in U.S. Pat. No. 5,876,995 to Bryan.

The antiperspirant is added to retard premature dissolution, degradation, dissolution or other removal of the carrier medium resulting from excessive perspiration, such as that resulting due to physical exertion. Any convenient antiperspirant agent known in the art may be added to the carrier base in sufficient quantities to prevent or retard perspiration. Aluminum zirconium glycine, zirconium aluminum glycine, aluminum chlorohydrate, and aluminum zirconium trichlorohydrex and the like are all suitable antiperspirant agents. These antiperspirant agents are effective when added in amounts ranging from about 1 to 60 weight percent, and more preferably in amounts ranging from about 15 to 30 weight percent.

In other aspects of the invention, methods for increasing pedestrian visibility that utilize the compositions described herein are provided. In one form, a suitable method first includes selection of which exposed body portions the pedestrian desires to color. The pedestrian then evenly applies a coating of the visibility-enhancing composition to those body portions of sufficient thickness to provide the desired level of coloration. The coating may be applies by hand or wiped or brushed on with a cloth, brush or other similar application technique known in the art. The pedestrian may then travel, exercise, or otherwise move as desired. In the event of prolonged exercise or travel, the coating may be renewed or "touched-up" as required. After exercising, the pedestrian washes the composition off of his body using water or soap and water.

EXAMPLE COMPOSITION 1

A visibility-enhancing composition may be made by combining a thickened propylene glycol carrier medium with an orange food dye chromophore and an aluminum-containing antiperspirant. The composition includes, on a weight basis, about 30–90% carrier medium, about 5–40% chromophore, and about 1–25% antiperspirant. Prior to combining the propylene glycol carrier medium with the other components of the composition, it can be advantageously thickened to have a viscosity of about 4000 centipoise.

EXAMPLE COMPOSITION 2

A visibility-enhancing composition may be made by combining a thickened glycerin carrier medium with a bioluminescent luciferin chromophore and an aluminum chlorohydrate antiperspirant. The composition includes, on a weight basis, about 20–70% carrier medium, about 15–80% chromophore, and about 10–40% antiperspirant.

EXAMPLE COMPOSITION 3

A visibility-enhancing composition may be made by combining a water-soluble silicone-glycol copolymer carrier medium with a water-soluble fluorescent reagent that fluoresces in the red-yellow region of the visible spectrum and an aluminum zirconium glycine antiperspirant. The composition includes, on a weight basis, about 35–80% carrier medium, about 10–50% chromophore, and about 10–25% antiperspirant.

While the invention has been illustrated and described in detail in the foregoing description, the same is to be considered as illustrative and not restrictive in character, it being understood that only the preferred embodiment has been shown and described and that all changes and modifications that come within the spirit of the invention are to be desired to be protected. In addition, all references cited herein are indicative of the level of skill in the art and are hereby incorporated by reference in their entirety.

What is claimed is:

1. A method for temporarily increasing the visibility of a pedestrian at night, comprising:
   a) selecting a portion of exposed skin to be colored; and
   b) applying a film of fluorescent colorant to the portion of selected exposed skin in an amount sufficient to cover the selected portion of skin;
      wherein the portion of exposed skin is sufficient to substantially increase the visibility of the pedestrian;
      wherein the fluorescent colorant includes an antiperspirant agent; and
      wherein the fluorescent colorant is non-white.

2. The method of claim 1 further comprising the step of:
   c) washing the colorant off with water.

3. The method of claim 1 wherein the colorant further comprises a carrier medium and a chromophore.

4. The method of claim 3 wherein the carrier medium is selected from the group consisting of creams, lotions, gels, suspensions, and emulsions.

5. The method of claim 1 wherein the fluorescent colorant is chosen from the group consisting of orange, yellow, red, pink, purple, and green.

6. A method for temporarily increasing the visibility of a person at night while exercising, comprising:
   a) exposing a substantial portion of skin;
   b) selecting a portion of exposed skin to be colored; and
   c) coloring the selected portion of exposed skin with a visibility-enhancing agent further comprising:
      a water-soluble carrier medium;
      a water-soluble, non-white fluorescent coloring agent; and
      an antiperspirant agent;
   wherein the water-soluble coloring agent is present in an amount sufficient to substantially increase the reflectivity of a wearer;
   wherein the antiperspirant agent is present in an amount sufficient to substantially prevent perspiration during exercise; and
   wherein the selected portion of exposed skin is sufficient to substantially increase the visibility of the person.

7. A method for temporarily increasing the visibility of a person stranded in a remote location, comprising:
   a) exposing a substantial portion of skin;
   b) selecting a portion of exposed skin to be colored; and
   c) coloring the selected portion of exposed skin with a visibility-enhancing agent further comprising:

a water-soluble carrier medium;
a water-soluble, non-white fluorescent coloring agent; and
an antiperspirant agent;
wherein the water-soluble, non-white fluorescent coloring agent is present in an amount sufficient to substantially increase the visibility of the person; and
wherein the selected portion of exposed skin is sufficient to substantially increase the visibility of the person.

8. The method of claim 7 wherein the method is practiced at night.

* * * * *